(12) United States Patent
Gren et al.

(10) Patent No.: US 6,911,217 B1
(45) Date of Patent: Jun. 28, 2005

(54) CONTROLLED RELEASE BEAD, A METHOD OF PRODUCING THE SAME AND MULTIPLE UNIT FORMULATION COMPRISING IT

(75) Inventors: Torkel Gren, Kalamazoo, MI (US); Anders Ringberg, Stockholm (SE); Martin Wikberg, Kullavik (SE); Randy J. Wald, Portage, MI (US)

(73) Assignee: Pharmacia AB, Stockholm (SE)

(*) Notice: Subject to any disclaimer, the term of this patent is extended or adjusted under 35 U.S.C. 154(b) by 0 days.

(21) Appl. No.: 09/763,281

(22) PCT Filed: Nov. 11, 1999

(86) PCT No.: PCT/SE99/02052

§ 371 (c)(1),
(2), (4) Date: May 5, 2001

(87) PCT Pub. No.: WO00/27364

PCT Pub. Date: May 18, 2000

(30) Foreign Application Priority Data

Nov. 11, 1998 (SE) .............................................. 9803871
Aug. 26, 1999 (WO) ............................... PCT/SE99/01463

(51) Int. Cl.⁷ ........................... A61K 9/00; A61K 9/52; A61K 9/54; A61K 9/56; A61K 31/135
(52) U.S. Cl. .................. 424/497; 424/489; 424/490; 424/493; 424/494; 424/495; 424/400; 424/451; 424/452; 424/457; 424/458; 424/459; 424/461; 424/462; 424/464; 424/465; 424/468; 514/648; 514/649
(58) Field of Search ................................. 424/458, 468, 424/472, 476, 480, 481, 482, 489, 490, 494, 495, 496, 497, 498

(56) References Cited

U.S. PATENT DOCUMENTS

| 5,645,858 A | * | 7/1997 | Kotwal et al. ............... 424/495 |
| 6,312,728 B1 | * | 11/2001 | Beiman et al. ............. 424/490 |

FOREIGN PATENT DOCUMENTS

| EP | A2061217 | 9/1982 | | |
| JP | 7-107450 | 1/1995 | | |
| JP | 7-275688 | 10/1995 | | |
| WO | A1-9601621 | 1/1996 | | |
| WO | A1-9629992 | 10/1996 | | |
| WO | WO 98/03067 | 1/1998 | .......... | A01N/33/18 |
| WO | WO 98/03067 A1 | * 1/1998 | .......... | A01N/33/18 |

* cited by examiner

Primary Examiner—Gollamudi S. Kishore
Assistant Examiner—Simon J. Oh

(57) ABSTRACT

A controlled release bead comprises: (i) a core unit of a substantially water-soluble or water-swellable inert material; (ii) a first layer on the core unit of a substantially water-insoluble polymer; (iii) a second layer covering the first layer and containing an active ingredient; and (iv) a third layer of polymer on the second layer effective for controlled release of the active ingredient, wherein the first layer is adapted to control water penetration into the core. A method of producing the controlled release bead is also disclosed.

24 Claims, 2 Drawing Sheets

Figure 1:
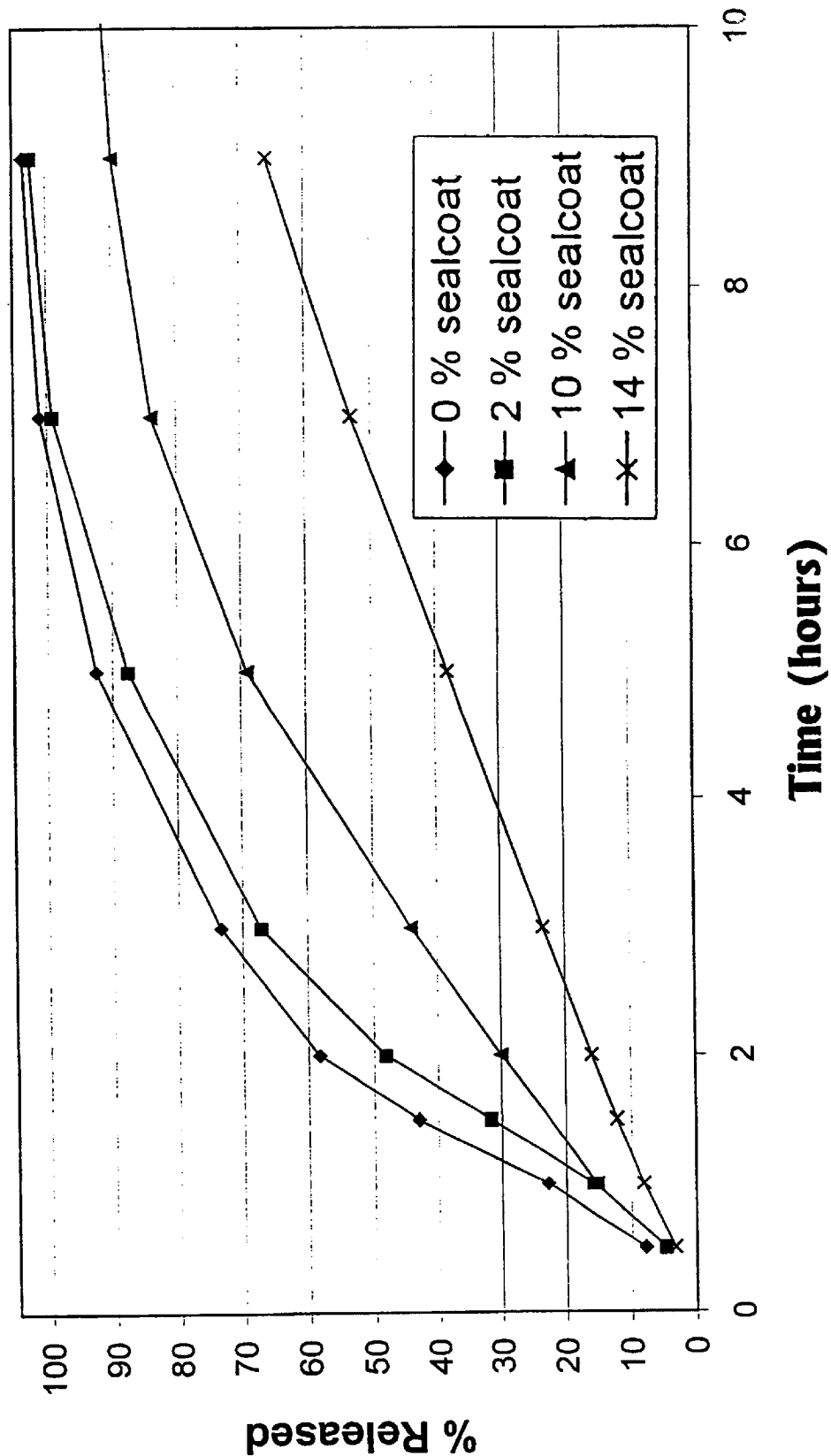

CONTROLLED RELEASE BEAD, A METHOD OF PRODUCING THE SAME AND MULTIPLE UNIT FORMULATION COMPRISING IT

This application is the national phase under 35 U.S.C. § 371 of PCT International Application No. PCT/SE99/02052 which has an International filing date of Nov. 11, 1999, which designated the United States of America.

The present invention relates to pharmaceutical controlled release beads comprising a drug, to a formulation containing said controlled release beads, and to a method of preparing said beads.

A common type of controlled release beads comprises an inert core, such as a sugar sphere, coated with an inner drug-containing layer and an outer membrane layer controlling drug release from the inner layer.

An example of such controlled release beads is described in U.S. Pat. No. 5,783,215 where each bead comprises (i) a core unit of a soluble or insoluble inert material, (ii) a first layer on the core unit comprising an active ingredient dispersed in a hydrophilic polymer, (iii) an optional second layer of hydrophilic polymer covering the first layer, and (iv) an outermost membrane layer effective for controlled release of the active ingredient.

In the above and similar controlled release beads it is not uncommon to apply a "sealcoat" in the form of a small amount (e.g. 1–3%) of a water-soluble polymer, such as hydroxypropylmethyl cellulose (HPMC) or polyvinylpyrrolidone (PVP), between the inert core and the layer containing the active ingredient. The purpose thereof is generally to isolate the drug from the core surface in the event that a drug-core chemical interaction is possible, and/or to smooth the surface of the inert core such that the surface area is more consistent from lot to lot to thereby improve the coating quality when the drug layer and the controlled release membrane layers are applied.

According to the present invention, it has now surprisingly been found that by applying a relatively thick layer of a water-insoluble polymer to the inert core as a sealcoat, several advantages may be obtained in addition to those mentioned above.

Firstly, in case of a soluble core like one of sugar, for example, the amount of time that the solution within the bead would be saturated with respect to drug may be maximized. Thus, by preventing the soluble core from being a reservoir for drug dissolution, the relative time that a saturated solution would remain within the bead during the release period can be increased considerably. This means that a substantially longer zero order drug release phase (the phase when the drug release rate is essentially constant) will be obtained (and less in the undesirable declining release rate phase). In other words, generally, the use of a thick sealcoat layer will permit the drug release profile to be altered in a predictable fashion, in particular for drugs with a moderate to high water solubility. Also, without drug migrating into the sealcoat, all drug will get released.

Secondly, the potential influence of the core material on drug release, in particular osmotic pressure or swelling of the core material which could potentially cause internal pressure and film rupture, may be minimized.

Thirdly, the substantial initial lag phase (no or very low amount of drug release early) that is generally observed with the prior art controlled release beads, especially for slower release formulations where the water influx is slower, may be substantially reduced or eliminated relatively independently of the steady state release rate.

Therefore, in a first aspect, the present invention provides a controlled release bead comprising:

(i) a core unit of a substantially water-soluble or water-swellable inert material having;

(ii) a first layer on the core unit of a substantially water-insoluble polymer;

(iii) a second layer covering the first layer and containing an active ingredient; and (iv) a third layer on the second layer of polymer effective for controlled release of the active ingredient, wherein said first layer is adapted to control water penetration into the core.

The term "control water penetration into the core" as used above means that the water influx to the core should be retarded in a controlled manner to such an extent that the drug release profile will be altered in a predictable fashion. Thus, while in many cases it may be preferred that the water penetration into the core is substantially or completely eliminated, a certain, controlled influx of water to the core may be acceptable in other cases.

The above-mentioned first layer of water-insoluble material may also serve to provide mechanical integrity to the core.

Optionally, the above-mentioned third, or controlled release layer is coated with one or more additional layers of water-soluble or insoluble polymer, e.g. a non-thermoplastic soluble polymer to decrease tackiness of the beads for subsequent processing, such as curing and filling into capsules, or a secondary functional coating, such as an enteric coating that delays the onset of drug release. Optionally, such an additional layer may contain drug for immediate release.

Usually, the first layer (ii) above constitutes more than about 2% (w/w) of the final bead composition, preferably more than about 3% (w/w), e.g. from about 3% to about 80% (w/w).

The amount of the second layer (ii) above usually constitutes from about 0.05 to about 60% (w/w), preferably from about 0. 1 to about 30% (w/w) of the final bead composition.

The amount of the third layer (iv) above usually constitutes from about 1 to about 50% (w/w), preferably from about 2 to about 25% (w/w) of the final bead composition.

The core unit typically has a size in the range of from about 0.05 to about 2 mm.

In a second aspect, the present invention provides a multiple unit formulation comprising said controlled release beads, such as a capsule or a tablet.

The cores are preferably of a water-soluble or swellable material, and may be any such material that is conventionally used as cores or any other pharmaceutically acceptable water-soluble or water-swellable material made into beads or pellets. Especially, the beads are spheres of sucrose/starch (Sugar Spheres NF), sucrose crystals, or extruded and dried spheres typically comprised of excipients such as microcrystalline cellulose and lactose.

The substantially water-insoluble material in the first, or sealcoat layer is generally a "GI insoluble" or "GI partially insoluble" film forming polymer (latex or dissolved in a solvent). As examples may be mentioned ethyl cellulose, cellulose acetate, cellulose acetate butyrate, polymethacrylates such as ethyl acrylate/methyl methacrylate copolymer (Eudragit NE-30-D) and ammonio methacrylate copolymer types A and B (Eudragit RL30D and RS30D), and silicone elastomers. Usually, a plasticizer is used together with the polymer. Exemplary plasticizers include: dibutylsebacate, propylene glycol, triethylcitrate, tributylcitrate, castor oil, acetylated monoglycerides, acetyl triethylcitrate, acetyl butylcitrate, diethyl phthalate, dibutyl phthalate, triacetin, fractionated coconut oil (medium-chain triglycerides).

The second layer containing the active ingredient may be comprised of the active ingredient (drug) with or without a polymer as a binder. The binder, when used, is usually hydrophilic but may be water-soluble or water-insoluble. Exemplary polymers to be used in the second layer containing the active drug are hydrophilic polymers such as polyvinylpyrrolidone (PVP), polyalkylene glycol such as polyethylene glycol, gelatine, polyvinyl alcohol, starch and derivatives thereof, cellulose derivatives, such as hydroxypropylmethyl cellulose (HPMC), hydroxypropyl cellulose, carboxymethyl cellulose, methyl cellulose, ethyl cellulose, hydroxyethyl cellulose, carboxyethyl cellulose, carboxymethylhydroxyethyl cellulose, acrylic acid polymers, polymethacrylates, or any other pharmaceutically acceptable polymer.

A wide variety of therapeutically active agents may be used in conjuction with the present invention. While the therapeutic agent usually is a low or medium dose drug, also high-dose drugs may be contemplated for use in the present invention. The therapeutic agent is preferably a soluble or moderately water-soluble drug (e.g. having a solubility corresponding to from less than 1 to about 30 ml of water per gram of solute at a temperature between 15° C. and 25° C.).

The ratio of drug to hydrophilic polymer in the second layer is usually in the range of from 1:100 to 100:1 (w/w).

Suitable polymers for use in the third layer, or membrane, for controlling the drug release may be selected from water-insoluble polymers or polymers with pH-dependent solubility, such as, for example, ethyl cellulose, hydroxypropylmethyl cellulose phthalate, cellulose acetate phthalate, cellulose acetate trimellitate, polymethacrylates, or mixtures thereof, optionally combined with plasticizers, such as those mentioned above. Optionally, the controlled release layer comprises, in addition to the polymers above, another substance(s) with different solubility characteristics, to adjust the permeability, and thereby the release rate, of the controlled release layer. Exemplary polymers that may be used as a modifier together with, for example, ethyl cellulose include: HPMC, hydroxyethyl cellulose, hydroxypropyl cellulose, methylcellulose, carboxymethylcellulose, polyethylene glycol, polyvinylpyrrolidone (PVP), polyvinyl alcohol, polymers with pH-dependent solubility, such as cellulose acetate phthalate or ammonio methacrylate copolymer and methacrylic acid copolymer, or mixtures thereof. Additives such as sucrose, lactose and pharmaceutical grade surfactants may also be included in the controlled release layer, if desired.

In a third aspect, the present invention provides a method for producing the controlled release beads and formulation, respectively. This method comprises the following steps:

a) providing a core unit of a substantially water-soluble or water-swellable material;

b) applying a first layer of a substantially water-insoluble polymer to said core;

c) applying onto said first layer, a second layer comprising an active ingredient and optionally a polymer binder; and d) applying onto said second layer, a third polymer layer effective for controlled release of the active ingredient;

wherein the amount of material in said first layer is selected to provide a layer thickness that permits control of water penetration into the core.

Optionally, the method comprises the further step of applying one or more additional polymer layers to the core as has been mentioned above.

The preparation of the multiple unit formulation comprises the additional step of transforming the prepared beads into a pharmaceutical formulation, such as by filling a predetermined amount of the beads into a capsule, or compressing the beads into tablets.

The layering or coating operations are preferably performed by spraying a solution or dispersion of the respective layer materials onto the core, preferably in a fluid bed coating apparatus.

After the final coating step, the beads are optionally "cured", usually in a fluid bed system or in a tray dryer system, by heating to a temperature of about 30–80° C., for 30 to 180 minutes, for example. Suitably, the beads are then cooled below about 35° C. before stopping the process.

The pharmaceutical formulation of the invention may be administered orally.

An exemplary class of compounds which may be used as active ingredients in the present invention comprises the 3,3-diphenylpropylamines disclosed in U.S. Pat. Nos. 5,382,600, 5,559,269 and 5,686,464 (the entire diclosures of which are incorporated by reference herein) and having the general formula:

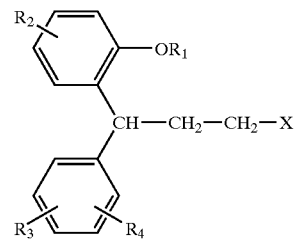

wherein $R_1$ signifies hydrogen or methyl; $R_2$, $R_3$ and $R_4$ independently signify hydrogen, methyl, methoxy, hydroxy, hydroxymethyl, carbamoyl, sulphamoyl or halogen; and X represents a tertiary amino group —$NR_5,R_6$, wherein $R_5$ and $R_6$ signify non-aromatic hydrocarbyl groups, which may be the same or different, especially $C_{1-6}$-alkyl or adamantyl, and which together contain at least three, preferably at least four carbon atoms, and each of which may carry a hydroxy substituent, and wherein $R_5$ and $R_6$ may form a ring together with the amine nitrogen, preferably a non-aromatic ring having no heteroatom other than the amine nitrogen, their salts with physiologically acceptable acids and, when the compounds can be in the form of optical isomers, the racemic mixture and the individual enantiomers. An exemplary specific compound is tolterodine, i.e. (R)-N,N-diisopropyl-3-(2-hydroxy-5-methylphenyl)-3-phenylpropanamine, as well as the corresponding (S)-enantiomer, the racemate and the active 5-hydroxymethyl metabolites, prodrug forms and pharmaceutically acceptable salts thereof.

Useful analogues to the above compounds are disclosed in WO 98/43942 (the full diclosure of which is incorporated by reference herein).

The above as well as the latter compounds have anticholinergic activity and may be used for treating, inter alia, urinary disorders including overactive urinary bladder.

The overactive bladder condition gives rise to urinary frequency, urgency and/or urge incontinence. Overactive bladder disorders also include nocturia, i.e. awakening at night to urinate. While overactive bladder is often associated with detrusor muscle instability, disorders of bladder function may also be due to neuropathy of the central nervous system (detrusor hyperreflexia) including spinal cord and brain lesions, such as multiple sclerosis and stroke. Overactive bladder symptoms may also result from, for example, male bladder outlet obstruction (usually due to prostatic hypertrophy), interstitial cystitis, local edema and irritation due to focal bladder cancer, radiation cystitis due to radiotherapy to the pelvis, and cystitis. The compounds also have spasmolytic activity and may be useful for treating gastrointestinal disorders, including gastrointestinal hyperactivity.

Specifically, the beads and multiple unit formulation, respectively, according to the present invention have proved to be very suitable for administering the above-mentioned drug tolterodine, the chemical name of which is (R)-N,N-diisopropyl-3-(2-hydroxy-5-methylphenyl)-3-phenylpropanamine, and would likewise be suitable for its related compounds, i.e. the major, active metabolite of tolterodine, i.e. (R)-N,N-diisopropyl-3-(2-hydroxy-5-hydroxymethylphenyl)-3-phenylpropanamine; the corresponding (S)-enantiomer to tolterodine, i.e. (S)-N,N-diisopropyl-3-(2-hydroxy-5-methylphenyl)-3-phenylpropanamine; the 5-hydroxymethyl metabolite of the (S)-enantiomer, i.e. (S)-N,N-diisopropyl-3-(2-hydroxy-5-hydroxymethylphenyl)-3-phenylpropanamine; as well as the corresponding racemate to tolterodine, i.e. (R,S)-N,N-diisopropyl-3-(2-hydroxy-5-methylphenyl)-3-phenylpropanamine; and prodrug forms and pharmacologically acceptable salts thereof.

Tolterodine is marketed for the treatment of unstable or overactive urinary bladder with symptoms including urge incontinence, urgency and urinary frequency. The 5-hydroxymethyl metabolite of tolterodine mentioned above contributes significantly to the therapeutic effect of tolterodine. A salient feature of tolterodine is that it has considerably less side-effects than the previously conventionally used drug, oxybutynin, especially regarding the propensity to cause dry mouth.

When tolterodine is the active ingredient in the controlled release bead, the fraction of active ingredient that is released in vitro is preferably not more than about 30% after 1 hour, from about 40 to about 85% after 3 hours, and not less than about 80% after 7 hours.

Administration of the controlled release formulation according to the present invention permits a well controlled release of tolterodine, and thereby a substantially constant serum level of active moiety or moieties to be maintained in the patient for at least 24 hours.

By the term "active moiety or moities" is meant, in the case of tolterodine and its related compounds, the sum of free or unbound (i.e. not protein bound) concentrations of (i) tolterodine and active metabolite thereof, when tolterodine (or prodrug form) is administered; or (ii) tolterodine and active metabolite thereof and/or (S)-enantiomer to tolterodine and active metabolite thereof, when the corresponding racemate (or prodrug form) is administered; or (iii) active metabolite, when the (R)-5-hydroxymethyl metabolite of tolterodine (or prodrug form) is administered; or (iv) (S)-enantiomer to tolterodine and active metabolite thereof, when the (S)-enantiomer (or prodrug) is administered; or (v) active (S)-metabolite, when the (S)-5-hydroxymethyl metabolite is administered.

The term "substantially constant" with respect to the serum level of active moiety or moieties means that the serum profile after administration of the controlled release formulation does essentially not exhibit any peak values. This may also be expressed mathematically by reference to the "fluctuation index" (FI) for the serum concentration of (unbound) active moiety (or sum of active moities when relevant), where the fluctuation index FI is calculated as $$FI=(C_{max}-C_{min})/AUC\tau/\tau$$

wherein Cmax and Cmin are the maximum and minimum concentrations, respectively, of active moiety, $AUC\tau$ is the area under the serum concentration profile (concentration vs time curve), and $\tau$ is the length of the dosage interval during the time $\tau$. The controlled release formulation according to the present invention readily permits a mean fluctuation index (for n being at least 30) that is not higher than about 2.0, more preferably not higher than about 1.5, particularly not higher than about 1.0, for example not higher than about 0.8.

For tolterodine and its 5-hydroxymethyl metabolite, the 24-hour exposure, expressed as AUC unbound active moiety (tolterodine plus metabolite) is usually in the range of from about 5 to about 150 nM*h, preferably from about 10 to about 120 nM*h, depending on the dosage needed by the particular patient. The indicated limits are based upon calculation of the unbound concentrations of active moiety assuming a fraction unbound of 3.7% for tolterodine and 36% for the 5-hydroxymethyl metabolite (Nilvebrant, L., et al., Life Sciences, Vol. 60, Nos. 13/14 (1997) 1129–1136).

Correspondingly, for tolterodine and its 5-hydroxymethyl metabolite, the average unbound (blood) serum or plasma levels of active moiety (tolerodine plus metabolite) are usually in the range of about 0.2 to about 6.3 nM, preferably in the range of about 0.4 to about 5.0 nM.

Tolterodine, its corresponding (S)-enantiomer and racemate and the preparation thereof are described in e.g. the above-mentioned U.S. Pat. No. 5,382,600. For a description of the active (R)-5-hydroxymethyl metabolite of tolterodine (as well as the (S)-5-hydroxymethyl metabolite), it may be referred to the above-mentioned U.S. Pat. No. 5,559,269.

The (S)-enantiomer, its non-cholinergic spasmolytic activity and use in the treatment of urinary and gastrointestinal disorders are described in WO 98/03067.

Figure 2:
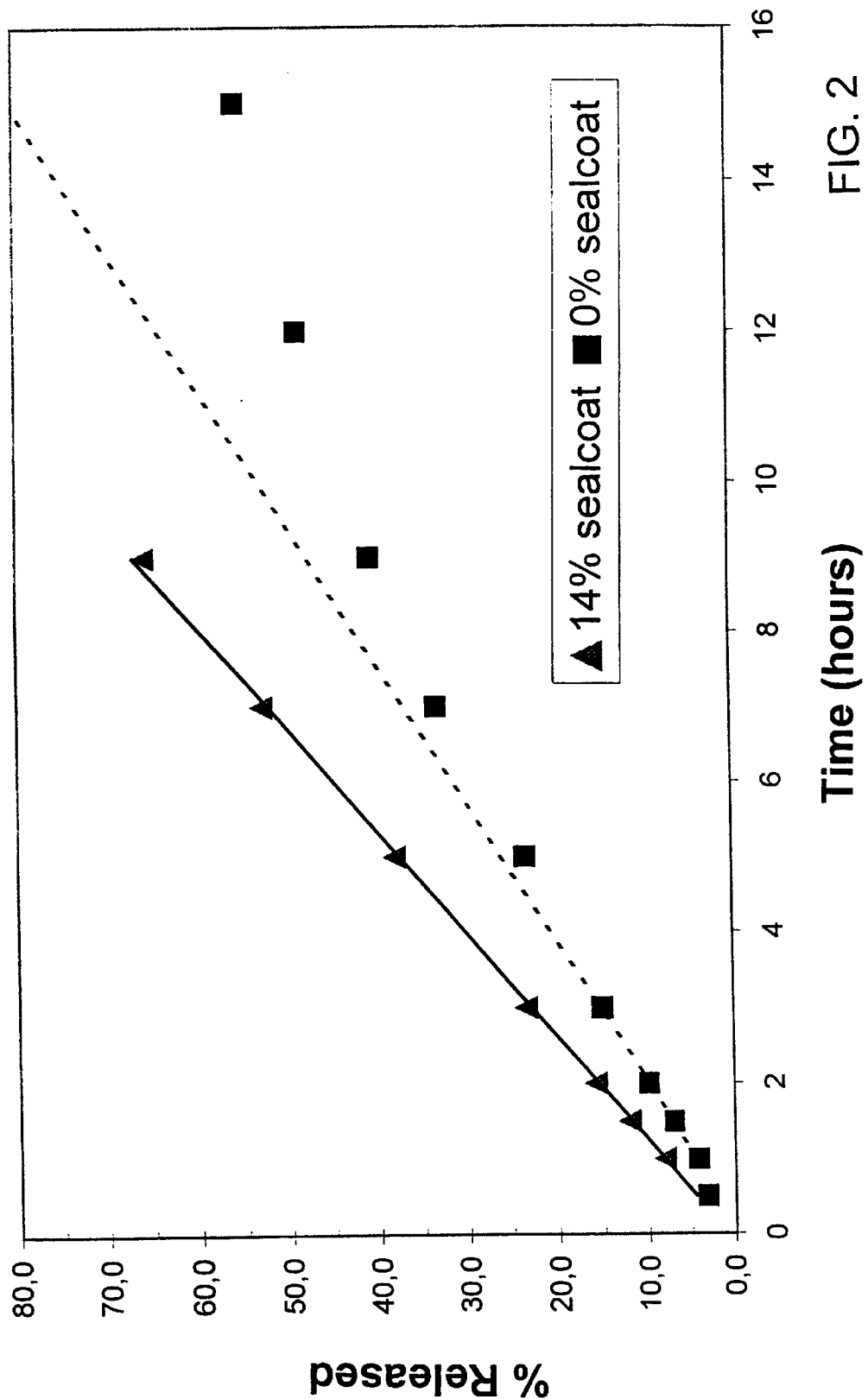

The invention will now be described in more detail by the following non-limiting Examples. Reference will be made to the accompanying drawings, wherein:

FIG. 1 is a diagram showing the fraction of released drug versus time for tolterodine beads according to Example I below with different sealcoat thicknesses; and FIG. 2 is a diagram showing the fraction of released drug versus time for tolterodine beads according to Example 1 below with 14% (w/w) and 0% (w/w) seal coat, respectively. The polymer composition in the third layer of the beads with 0% sealcoat has been adjusted in order to produce approximately similar initial drug release as from beads with 14% sealcoat.

EXAMPLE 1

An exemplary bead containing tolterodine L-tartrate as active ingredient has the following structure:

Core: Starch-containing sugar sphere of about 0.8 mm diameter (commercially available); comprises 73% w/w of the final bead; purpose: coating substrate;

First layer: Surelease® "sealcoat" (Surelease® is an aqueous film-coating dispersion, about 25% solids, consisting primarily of ethylcellulose plasticized with fractionated coconut oil, and manufactured by Colorcon, Inc, USA); comprises about 12% w/w of the final bead; purpose: to provide more consistent core surface; during drug release phase maximize time that drug is saturated inside bead and minimize osmotic effects; control drug release rate together with the third layer;

Second layer: Tolterodine L-tartrate/ hydroxypropylmethylcellulose (HPMC); comprises about 3% w/w of the final bead; ratio of Tolterodine:HPMC is 5:1; purpose: drug supply;

Third layer: Surelease®/HPMC; comprises about 12% w/w of the final bead; ratio of Surelease®:HPMC is 6:1; purpose: drug release rate control;

Beads with a three-layer coating having the above characteristics were prepared as follows:

1200 g of sugar spheres, 20–25 mesh, were charged into a Wurster fluid bed and sequentially coated at a nominal product temperature of 36 to 40° C. with the following three coating liquids:

(1) a Surelease® sealcoating liquid prepared by mixing 788 g of Surelease® with 563 g of purified water;
(2) a drug-containing solution prepared by first dissolving 35.0 g of tolterodine L-tartrate in 2190 g of purified water, and then mixing the solution with 6.6 g of hydroxypropylmethyl cellulose (HPMC) 5 cP; and
(3) a sustained release coating liquid prepared by mixing 29 g of HPMC 5 cP with 375 g of purified water, and then mixing with 695 g of Surelease®.

After tray drying for 3 hours at 70° C., the coated spheres were filled into size #4 or size #3 hard gelatin capsules to obtain 2 mg and 4 mg tolterodine L-tartrate capsules, respectively, of the composition:

|  | 2 mg capsule | 4 mg capsule |
| --- | --- | --- |
| Tolterodine L-tartrate | 2.0 mg | 4.0 mg |
| sugar spheres, 20–25 mesh | 68.6 mg | 137.2 mg |
| Surelease ® | 21.2 mg | 42.4 mg |
| HPMC 5cP | 2.0 mg | 4.0 mg |

Optionally, a fourth layer may be applied to the bead before drying by Wurster coating.

Fourth layer: HPMC; comprises about 1% w/w of the final bead; purpose: decrease tackiness of beads for subsequent processing (curing and capsule filling).

In the case of the above described bead, such a fourth layer may be applied with a coating solution prepared by dissolving 16.4 g of HPMC in 234 g of water.

Study of Effect of Sealcoat Thickness

The effect of the sealcoat thickness on drug release was tested as follows. Four lots of 20–25 mesh beads were prepared that contained (i) a Surelease® sealcoat layer at 0, 2, 10 or 14% level, (ii) an HPMC/drug (tolterodine L-tartrate) layer at 4% level (drug:HPMC ratio=5:4), (iii) a Surelease®/HPMC layer at 10% level (Surelease®:HPMC ratio=6:1 ratio), and (iv) a final HPMC layer at 1%. These were prepared essentially as described above and cured 1 hr at 70 ° C.

Note that the coating level for layer (i) is expressed relative to the sum of the core plus sealcoat while coating levels for layers (ii–iv) are expressed relative to the final coated bead weight.

A fifth lot of beads was also manufactured identical to the 0% sealcoat lot described above except that the third coating layer was modified (increase in the Surelease®: HPMC layer from a 6:1 to a 11:1) such that the initial drug release rate was similar to the 14% sealcoat formulation described above.

The in vitro drug release at 37° C. in phosphate buffer pH 6.8 with addition of 0.22 M potassium chloride was measured. The USP dissolution test apparatus I was used. The results are shown in the diagrams in FIG. 1 and 2. As shown in FIG. 1, as the sealcoat layer gets thicker, the drug release rate both decreases and becomes more zero-order.

FIG. 2 shows the comparison of the 0% sealcoat formulation (11:1 Surelease®: HPMC) to the 14% sealcoat (6:1 the Surelease®: HPMC). It can be seen that, after a slight lag period observed by the 0% sealcoated beads, the initial drug release rates are similar. However, after approximately 15–20% of the drug is released, the release rate from beads with 0% sealcoat beads falls while release rate from the 14% sealcoat remains extremely zero order. Indeed, for the 0% sealcoat beads the release rate between 45–60% is only approximately half of the initial (first 20%) release rate. Comparatively, for the 14% sealcoat lot, the release rate between 45–60% range is identical to the rate over the first 20%.

In an analogous manner to the procedure described in Example 1 above, other exemplary bead formulations containing tolterodine L-tartrate as the active ingredient were prepared as described in Examples 2 and 3 below.

EXAMPLE 2

400 g of sugar spheres (20–25 mesh, Edward Mendell Co, USA) were charged into a top-spray fluid bed coater (Nica, Sweden) and coated with Surelease® and thereafter cured in a drying cabinet at 70° C. for 5 hours.

A solution of tolterodine-L-tartrate and hydroxypropyl cellulose (HPC) in water was sprayed onto the coated cores.

The spheres obtained were then coated with a mixture of ethylcellulose, hydroxypropylcellulose and triethylcitrate (plasticizer). The coating materials were dissolved in a mixture of dichlormethane and ethanol.

The resulting beads had the following composition expressed as % (w/w):

| Sugar spheres | 75.7 |
| --- | --- |
| Surelease ® | 13 |
| Tolterodine L-tartrate | 4.9 |
| HPC | 1.5 |
| Ethylcellulose | 4.3 |
| Triethyl citrate | 0.6 |

The obtained spheres showed extended release of tolterodine L-tartrate over at least 10 hours. The release rate was essentially constant.

EXAMPLE 3

4800 g of sugar spheres (18–20 mesh, Mendell, USA) were coated in a Wurster fluid bed with Surelease® to a theoretical weight gain of 10% and thereafter cured in a drying cabinet at 60° C. for 6 hours.

A solution of tolterodine L-tartrate and hydroxypropylmethyl cellulose (HPMC) in water was sprayed onto 1200 g of the cured sphere cores.

1000 g of the obtained spheres were then coated by spraying with an aqueous dispersion of a cross-linked latex of hydroxyl-end blocked polydimethylsiloxan (PDMS, Dow Corning; USA) and colloidal silica (Dow Corning, USA) to a theoretical weight gain of 15%.

The resulting beads had the following composition expressed as % (w/w):

| | |
|---|---|
| Sugar spheres | 76 |
| Surelease ® | 7.8 |
| Tolterodine L-tartrate | 2.8 |
| HPMC | 0.4 |
| PDMS | 8.7 |
| Colloidal silica | 4.3 |

The obtained spheres showed extended release of tolterodine L-tartrate over at least 11 hours. The release rate was nearly constant.

While the invention has been described above with reference to specific embodiments thereof, it is not restricted thereto in any way whatsoever. On the contrary, as will be understood by those skilled in the art, various changes, modifications, substitutions and omissions can be made without departing from the basic concept of the invention as defined in the claims which follow.

What is claimed is:

1. A controlled-release bead comprising:
   (i) a core unit of a substantially water-soluble or water-swellable inert material;
   (ii) a first layer on the core unit of a substantially water-insoluble polymer;
   (iii) a second layer covering the first layer that contains an active ingredient, comprising compounds of the general formula

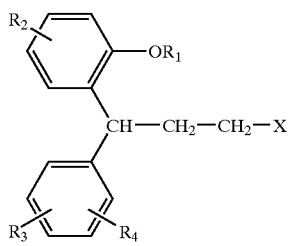

wherein $R_1$ signifies hydrogen or methyl; $R_2$, $R_3$ and $R_4$ independently signify hydrogen, methyl, methoxy, hydroxy, hydromethyl, carbamoyl, sulphamoyl or halogen; and X represents a tertiary amino group —$NR_5$, $R_6$, wherein $R_5$ and $R_6$ signify non-aromatic hydrocarbyl groups, which may be the same or different, especially $C_{1-6}$-alkyl or adamantyl, and which together contain at least three, preferably at least four carbon atoms, and each of which may carry a hydroxy substituent, and wherein $R_5$ and $R_6$ may form a ring together with the amine nitrogen, preferably a non-aromatic ring having no heteroatom other than the amine nitrogen, their salts with physiologically acceptable acids and, when the compounds can be in the form of optical isomers, the racemic mixture and the individual enantiomers, and
   (iv) a third layer of polymer on the second layer effective for the controlled release of the active ingredient,
   wherein said first layer is adapted to control water penetration into the core,
   and wherein the controlled-release bead provides a mean fluctuation index of said serum level of the active moiety or moieties that is not higher than about 2.0, said fluctuation index, FI, being defined as FI=(Cmax−Cmin)/AUCτ/τ, wherein Cmax and Cmin are the maximum and minimum concentrations, respectively, of the active moiety or moieties, AUCτ is the area under the serum concentration profile, and τ is the length of the dosage interval.

2. The bead according to claim 1, wherein the amount of polymer in said first layer comprises from about 2.0% w/w to about 50% w/w of the bead and is sufficient to substantially retard water penetration into the core.

3. The bead according to claim 1 wherein the thickness of said first layer is from about 1.0 μm to about 100 μm and is sufficient to affect the drug release rate from the bead.

4. The bead according to claim 1, wherein the amount of the first layer constitutes more than 2% (w/w) of the final bead composition.

5. The bead according to claim 1, wherein the amount of said second layer constitutes from about 0.05 to about 60% (w/w).

6. The bead according to claim 1, wherein the amount of said third layer constitutes from about 1 to about 50% (w/w) of the final bead composition.

7. The bead according to claim 1, wherein said third polymer layer is coated with a fourth layer of a water-soluble polymer for an additional functional coating.

8. The bead according to claim 1, wherein said active ingredient is selected from tolterodine, the 5-hydroxymethyl metabolite of tolterodine, the (S)-enantiomer of tolterodine, the 5-hydroxymethyl metabolite of the (S)-enantiomer of tolterodine, the racemate of tolterodine, its prodrug forms and pharmacologically acceptable salts thereof.

9. The bead according to claim 8, wherein said active ingredient is tolterodine or a pharmacologically acceptable salt thereof.

10. The bead according to claim 9, wherein the fraction of active ingredient that is released in vitro is not more than about 30% after 1 hour, from about 40 to about 85% after 3 hours, and not less than about 80% after 7 hours.

11. The bead according to claim 1, wherein the polymer material of said first layer comprises ethyl cellulose.

12. The bead according to claim 1, wherein said second layer comprises hydroxypropylmethyl cellulose as binder.

13. The bead according to claim 1, wherein the polymer material of said third layer comprises a combination of hydroxypropylmethyl cellulose and ethyl cellulose.

14. The bead according to claim 1, wherein the core unit has a size of about 0.05 to about 2 mm.

15. A multiple unit formulation comprising a controlled release bead according to claim 1.

16. The multiple unit formulation according to claim 15 which is a capsule.

17. A method of producing a controlled release bead according to claim 1, which method comprises the steps of:
   a) providing a core unit of a substantially water-soluble or water-swellable material;
   b) applying a first layer of a substantially water-insoluble polymer to said core;
   c) applying onto said first layer, a second layer comprising an active ingredient and optionally a polymer binder; and
   d) applying onto said second layer, a third polymer layer effective for the controlled release of the active ingredient;
   wherein the amount of material in said first layer is selected to provide a layer thickness that permits control of water penetration into the core.

18. A method for treating overactive bladder, which comprises administering a therapeutically effective amount of beads according to claim 1.

19. The method according to claim 18 wherein the active ingredient is tolterodine or a pharmacologically acceptable salt thereof.

20. A method for treating nocturia, which comprises administering a therapeutically effective amount of the beads according to claim 1.

21. The method according to claim 20, wherein the active ingredient is tolterodine or a pharmacologically acceptable salt thereof.

22. A method for treating gastrointestinal disorders, which comprises administering a therapeutically effective amount of beads according to claim 1.

23. A controlled release bead consisting essentially of:
(i) a core unit of a substantially water-soluble or water-swelled inert material;
(ii) a first layer on the core unit of a substantially water-insoluble polymer;
(iii) a second layer covering the first layer that contains an active ingredient comprising compounds of the general formula:

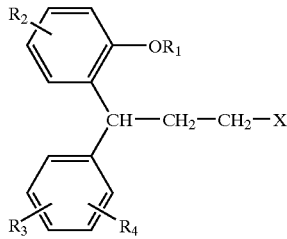

wherein $R_1$ signifies hydrogen or methyl; $R_2$, $R_3$ and $R_4$ independently signify hydrogen, methyl, methoxy, hydroxy, hydroxymethyl, carbamoyl, sulphamoyl or halogen; and X represents a tertiary amino group $-NR_5,R_6$ wherein $R_5$ and $R_6$ signify non-aromatic hydrocarbyl groups, which may be the same or different, especially $C_{1-6}$-alkyl or adamantyl, and which together contain at least three, preferably at least four carbon atoms, and each of which may carry a hydroxy substituent, and wherein $R_5$ and $R_6$ may form a ring together with the amine nitrogen, preferably a non-aromatic ring having no heteroatom other than the amine nitrogen, their salts with physiologically acceptable acids and, when the compounds can be in the form of optical isomers, the racemic mixture and the individual enantiomers; and (iv) a third layer of polymer on the second layer effective for the controlled release of the active ingredient.

24. A controlled release bead comprising:
(i) a core unit of a substantially water-soluble or water-swelled inert material;
(ii) a first layer of a substantially water-insoluble polymer on and in contact with the core unit;
(iv) (iii) a second layer covering the first layer that contains an active ingredient comprising compounds of the general formula:

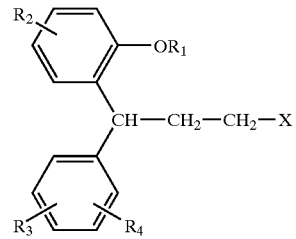

wherein $R_1$ signifies hydrogen or methyl; $R_2$, $R_3$ and $R_4$ independently signify hydrogen, methyl, methoxy, hydroxy, hydroxymethyl, carbamoyl, sulphamoyl or halogen; and X represents tertiary amino groups $-NR_5,R_6$, wherein $R_5$ and $R_6$ signify non-aromatic hydrocarbyl groups, which may be the same or different, especially $C_{1-6}$-alkyl or adamantyl, and which together contain at least three, preferably at least four carbon atoms, and each of which may carry a hydroxy substituent, and wherein $R_5$ and $R_6$ may form a ring together with the amine, nitrogen, preferably a non-aromatic ring having no heteroatom other than the amine nitrogen, their salts with physiologically acceptable acids and, when the compounds can be in the form of optical isomers, the racemic mixture and the individual enantiomers; and (iv) a third layer of polymer on the second layer effective for the controlled release of the active ingredient;
wherein said first layer is adapted to control water penetration into the core.

* * * * *

UNITED STATES PATENT AND TRADEMARK OFFICE
CERTIFICATE OF CORRECTION

PATENT NO.    : 6,911,217 B1
DATED         : June 28, 2005
INVENTOR(S)   : Torkel Gren et al.

It is certified that error appears in the above-identified patent and that said Letters Patent is hereby corrected as shown below:

Column 9,
Line 43, "hydromethyl" should read -- hydroxymethyl --.

Signed and Sealed this

Fifteenth Day of November, 2005

JON W. DUDAS
*Director of the United States Patent and Trademark Office*